US008454532B2

(12) United States Patent
Hibner

(10) Patent No.: US 8,454,532 B2
(45) Date of Patent: Jun. 4, 2013

(54) CLUTCH AND VALVING SYSTEM FOR TETHERLESS BIOPSY DEVICE

(75) Inventor: John A. Hibner, Mason, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 75 days.

(21) Appl. No.: 12/944,037

(22) Filed: Nov. 11, 2010

(65) Prior Publication Data

US 2011/0054349 A1    Mar. 3, 2011

Related U.S. Application Data

(63) Continuation of application No. 11/964,811, filed on Dec. 27, 2007.

(51) Int. Cl.
*A61B 10/02* (2006.01)

(52) U.S. Cl.
USPC ........... 600/568; 600/562; 600/563; 600/564; 600/565; 600/567

(58) Field of Classification Search
USPC .................................................. 600/562–568
See application file for complete search history.

(56) References Cited

U.S. PATENT DOCUMENTS

| 737,293 A | 8/1903 | Summerteldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |

(Continued)

FOREIGN PATENT DOCUMENTS

| DE | 3924291 A1 | 1/1991 |
| DE | 4041614 CI | 10/1992 |

(Continued)

OTHER PUBLICATIONS

U.S. Appl. No. 60/869,736, filed Dec. 13, 2006, Ritchie.

(Continued)

*Primary Examiner* — Sean Dougherty
(74) *Attorney, Agent, or Firm* — Frost Brown Todd LLC

(57) ABSTRACT

A biopsy device may include a needle, a cutter, and a handpiece. A vacuum pump may be provided in the handpiece for providing a vacuum to the needle and/or to the cutter. A motor may be provided in the handpiece to drive the vacuum pump and/or the cutter. A biopsy device may also include a valving mechanism within the handpiece for selectively communicating a vacuum and/or atmospheric air to the needle. A clutching mechanism may selectively provide communication between a motor and the cutter. Portions of a valving mechanism and a clutching mechanism may be integrally formed. A clutching and valving mechanism may be driven by a first motor; and a cutter and vacuum pump by a second motor. A biopsy device may include batteries for powering motors. A biopsy device may thus provide vacuum and power from within a handpiece, such that the biopsy device is tetherless.

20 Claims, 9 Drawing Sheets

U.S. PATENT DOCUMENTS

| | | | |
|---|---|---|---|
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,776,346 A | 10/1988 | Beraha et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,213,110 A | 5/1993 | Kedem et al. |
| 5,225,763 A | 7/1993 | Krohn et al. |
| 5,234,000 A | 8/1993 | Hakky et al. |
| 5,236,334 A | 8/1993 | Bennett |
| 5,249,583 A | 10/1993 | Mallaby |
| 5,282,476 A | 2/1994 | Terwilliger |
| 5,282,477 A | 2/1994 | Bauer |
| 5,324,306 A | 6/1994 | Makower et al. |
| 5,334,183 A | 8/1994 | Wuchinich |
| 5,368,029 A | 11/1994 | Holcombe et al. |
| 5,368,045 A | 11/1994 | Clement et al. |
| 5,400,798 A | 3/1995 | Baran |
| 5,406,959 A | 4/1995 | Mann |
| 5,439,474 A | 8/1995 | Li |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,585 A | 2/1997 | Banik et al. |
| 5,602,449 A | 2/1997 | Krause et al. |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,150 A | 6/1999 | Sillman |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Bussard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,228,055 B1 | 5/2001 | Foerster et al. |
| 6,231,522 B1 | 5/2001 | Voegele et al. |
| 6,233,831 B1 | 5/2001 | Iida et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |

| | | |
|---|---|---|
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,436,054 B1 | 8/2002 | Viola et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |
| 6,554,779 B2 | 4/2003 | Viola et al. |
| 6,585,664 B2 | 7/2003 | Burdorff et al. |
| 6,585,694 B1 | 7/2003 | Smith et al. |
| 6,626,849 B2 | 9/2003 | Huitema et al. |
| 6,638,235 B2 | 10/2003 | Miller et al. |
| 6,656,133 B2 | 12/2003 | Voegele et al. |
| 6,659,105 B2 | 12/2003 | Burbank et al. |
| 6,659,338 B1 | 12/2003 | Dittmann et al. |
| 6,683,439 B2 | 1/2004 | Takano et al. |
| 6,689,072 B2 | 2/2004 | Kaplan et al. |
| 6,695,786 B2 | 2/2004 | Wang et al. |
| 6,712,773 B1 | 3/2004 | Viola |
| 6,712,774 B2 | 3/2004 | Voegele et al. |
| 6,730,044 B2 | 5/2004 | Stephens et al. |
| 6,752,768 B2 | 6/2004 | Burdorff et al. |
| 6,753,671 B1 | 6/2004 | Harvey |
| 6,758,824 B1 | 7/2004 | Miller et al. |
| 6,764,495 B2 | 7/2004 | Lee et al. |
| 6,832,990 B2 | 12/2004 | Kortenbach et al. |
| 6,849,080 B2 | 2/2005 | Lee et al. |
| 6,908,440 B2 | 6/2005 | Fisher |
| D508,458 S | 8/2005 | Solland et al. |
| 6,926,676 B2 | 8/2005 | Turturro et al. |
| 6,984,213 B2 | 1/2006 | Horner et al. |
| 7,025,732 B2 | 4/2006 | Thompson et al. |
| D525,583 S | 7/2006 | Vu |
| 7,153,274 B2 | 12/2006 | Stephens et al. |
| 7,189,206 B2 | 3/2007 | Quick et al. |
| 7,189,207 B2 | 3/2007 | Viola |
| 7,219,867 B2 | 5/2007 | Kalis et al. |
| 7,226,424 B2 | 6/2007 | Ritchart et al. |
| 7,276,032 B2 | 10/2007 | Hibner |
| 7,278,970 B2 * | 10/2007 | Goldenberg ................ 600/564 |
| 7,328,794 B2 | 2/2008 | Lubs et al. |
| 7,347,829 B2 | 3/2008 | Mark et al. |
| 7,374,544 B2 | 5/2008 | Greeman et al. |
| 7,397,654 B2 | 7/2008 | Mori |
| 7,402,140 B2 | 7/2008 | Spero et al. |
| 7,405,536 B2 | 7/2008 | Watts |
| 7,407,054 B2 | 8/2008 | Seiler et al. |
| 7,419,472 B2 | 9/2008 | Hibner et al. |
| 7,432,813 B2 | 10/2008 | Postma |
| 7,442,171 B2 | 10/2008 | Stephens et al. |
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,662,109 B2 | 2/2010 | Hibner |
| 7,670,299 B2 | 3/2010 | Beckman et al. |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,758,515 B2 | 7/2010 | Hibner |
| 7,762,961 B2 | 7/2010 | Heske et al. |
| 7,828,746 B2 | 11/2010 | Teague |
| 7,828,748 B2 | 11/2010 | Hibner |
| 7,837,630 B2 * | 11/2010 | Nicoson et al. ............... 600/562 |
| 7,883,476 B2 | 2/2011 | Miller et al. |
| 8,251,917 B2 | 8/2012 | Almazan |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0045840 A1 | 4/2002 | Voegele et al. |
| 2002/0065474 A1 | 5/2002 | Viola |
| 2002/0067151 A1 | 6/2002 | Tanishita |
| 2002/0068878 A1 | 6/2002 | Jasonni et al. |
| 2002/0082518 A1 | 6/2002 | Weiss et al. |
| 2002/0107043 A1 | 8/2002 | Adamson et al. |
| 2002/0120210 A1 * | 8/2002 | Voegele ................ 600/564 |
| 2002/0138020 A1 * | 9/2002 | Pflueger ................ 600/562 |
| 2002/0151822 A1 | 10/2002 | Burdorff et al. |
| 2002/0156395 A1 | 10/2002 | Stephens et al. |
| 2003/0130593 A1 | 7/2003 | Gonzalez |
| 2003/0130677 A1 | 7/2003 | Whitman et al. |
| 2003/0144606 A1 | 7/2003 | Kadziauskas et al. |
| 2003/0163142 A1 | 8/2003 | Paltieli et al. |
| 2003/0195434 A1 * | 10/2003 | Voegele ................ 600/564 |
| 2003/0199753 A1 | 10/2003 | Hibner et al. |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0186393 A1 | 9/2004 | Leigh et al. |
| 2004/0215103 A1 | 10/2004 | Mueller, Jr. et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma de la Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0065453 A1 | 3/2005 | Shabaz et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0149163 A1 | 7/2006 | Hibner et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0241515 A1 | 10/2006 | Jones et al. |
| 2006/0258956 A1 | 11/2006 | Haberstich et al. |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0032742 A1 | 2/2007 | Monson et al. |
| 2007/0073326 A1 | 3/2007 | Miller et al. |
| 2007/0090788 A1 | 4/2007 | Hansford et al. |
| 2007/0106176 A1 | 5/2007 | Mark et al. |
| 2007/0118048 A1 * | 5/2007 | Stephens et al. ............ 600/564 |
| 2007/0118049 A1 | 5/2007 | Viola |
| 2007/0149894 A1 | 6/2007 | Heske et al. |

| | | | |
|---|---|---|---|
| 2007/0161925 A1 | 7/2007 | Quick et al. |
| 2007/0167782 A1 | 7/2007 | Callahan et al. |
| 2007/0213590 A1 | 9/2007 | Squicciarini |
| 2007/0213630 A1 | 9/2007 | Beckman et al. |
| 2007/0213632 A1 | 9/2007 | Okazaki et al. |
| 2007/0213755 A1 | 9/2007 | Beckman et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0270710 A1 | 11/2007 | Frass et al. |
| 2007/0276288 A1 | 11/2007 | Khaw |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heilser |
| 2008/0021488 A1 | 1/2008 | Berberich |
| 2008/0030170 A1 | 2/2008 | Dacquay et al. |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0146962 A1 | 6/2008 | Richie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson et al. |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bickenbach |
| 2008/0215056 A1 | 9/2008 | Miller et al. |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0228103 A1 | 9/2008 | Ritchie et al. |
| 2008/0228104 A1 | 9/2008 | Uber et al. |
| 2008/0232604 A1 | 9/2008 | Dufresne et al. |
| 2008/0234715 A1 | 9/2008 | Pesce et al. |
| 2008/0281225 A1 | 11/2008 | Spero et al. |
| 2008/0287826 A1 | 11/2008 | Videback et al. |
| 2008/0306406 A1 | 12/2008 | Thompson et al. |
| 2008/0308607 A1 | 12/2008 | Timm et al. |
| 2008/0319341 A1 | 12/2008 | Taylor et al. |
| 2009/0030405 A1 | 1/2009 | Quick et al. |
| 2009/0062624 A1 | 3/2009 | Neville |
| 2009/0082695 A1 | 3/2009 | Whitehead |
| 2009/0125062 A1 | 5/2009 | Arnin |
| 2009/0137927 A1 | 5/2009 | Miller |
| 2009/0171243 A1 | 7/2009 | Hibner et al. |
| 2009/0227893 A1 | 9/2009 | Coonahan et al. |
| 2010/0030020 A1 | 2/2010 | Sanders et al. |
| 2010/0063416 A1 | 3/2010 | Cicenas et al. |
| 2010/0152611 A1 | 6/2010 | Parihar et al. |
| 2010/0160820 A1 | 6/2010 | Weikel, Jr. et al. |
| 2010/0210966 A1 | 8/2010 | Videback |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |
| 2010/0317998 A1 | 12/2010 | Hibner et al. |
| 2011/0152715 A1 | 6/2011 | Delap et al. |
| 2011/0160611 A1 | 6/2011 | Ritchart et al. |

FOREIGN PATENT DOCUMENTS

| | | |
|---|---|---|
| DE | 10034297 A1 | 4/2001 |
| DE | 10026303 A1 | 2/2002 |
| DE | 20209525 U1 | 11/2002 |
| DE | 10235480 A1 | 2/2004 |
| EP | 0433717 A1 | 6/1991 |
| EP | 0890339 A1 | 1/1999 |
| EP | 0995400 A2 | 4/2000 |
| EP | 1074271 A2 | 2/2001 |
| EP | 1 520 518 | 4/2005 |
| EP | 1579809 A1 | 9/2005 |
| EP | 1665989 A2 | 6/2006 |
| EP | 2095772 A1 | 9/2009 |
| EP | 2106750 A2 | 10/2009 |
| FR | 1345429 A | 12/1963 |
| FR | 2739293 A1 | 4/1997 |
| GB | 2 018 601 | 10/1979 |
| JP | H10508504 A | 8/1998 |
| JP | 2005530554 A | 10/2005 |
| JP | 2006509545 A | 3/2006 |
| JP | 2006825907 A | 12/2006 |
| JP | 2007502159 A | 2/2007 |
| RU | 2021770 | 10/1994 |
| WO | WO 96/28097 A1 | 9/1996 |
| WO | WO 98/25522 A1 | 6/1998 |
| WO | WO 98/31285 A1 | 7/1998 |
| WO | WO 98/35615 A1 | 8/1998 |
| WO | WO 98/46290 A1 | 10/1998 |
| WO | WO 99/33501 A1 | 7/1999 |
| WO | WO 00/04832 A1 | 2/2000 |
| WO | WO 00/30546 A1 | 6/2000 |
| WO | WO 00/59378 A2 | 10/2000 |
| WO | WO 01/72230 A1 | 10/2001 |
| WO | WO 02/22023 A1 | 3/2002 |
| WO | WO 02/32318 A1 | 4/2002 |
| WO | WO 02/069808 A2 | 9/2002 |
| WO | WO 2004/075728 | 9/2004 |
| WO | WO 2005/013830 A1 | 2/2005 |
| WO | WO 2006/005342 | 1/2006 |
| WO | WO 2006/005344 A1 | 1/2006 |
| WO | WO 2006/015302 A1 | 2/2006 |
| WO | WO 2007/047128 A1 | 4/2007 |
| WO | WO 2007/095330 A2 | 8/2007 |
| WO | WO 2007/112751 A2 | 10/2007 |
| WO | WO 2008/021687 A1 | 2/2008 |
| WO | WO 2008/040812 A1 | 4/2008 |
| WO | WO 2008/131362 A2 | 10/2008 |

OTHER PUBLICATIONS

U.S. Appl. No. 60/874,792, filed Dec. 13, 2006, Hibner et al.
European Search Report dated Apr. 13, 2010 for Application No. EP 08254140.
Prato, A.P., et al., "Solo-RBT: A New Instrument for Rectal Suction Biopsies in the Diagnosis of Hirschsprung's Disease", Journal of Pediatric Surgery, Sep. 2001, vol. 36, No. 9, pp. 1364-1366.

* cited by examiner

CLUTCH AND VALVING SYSTEM FOR TETHERLESS BIOPSY DEVICE

PRIORITY

This application is a continuation of U.S. patent application Ser. No. 11/964,811, entitled "Clutch and Valving System for Tetherless Biopsy Device," filed Dec. 27, 2007, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,764, entitled "Vacuum Timing Algorithm for Biopsy Device," filed Nov. 20, 2007. The disclosure of each of the above-cited U.S. Patents, U.S. Patent Application Publications, U.S. Provisional Patent Applications, and U.S. Non-Provisional Patent Application is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
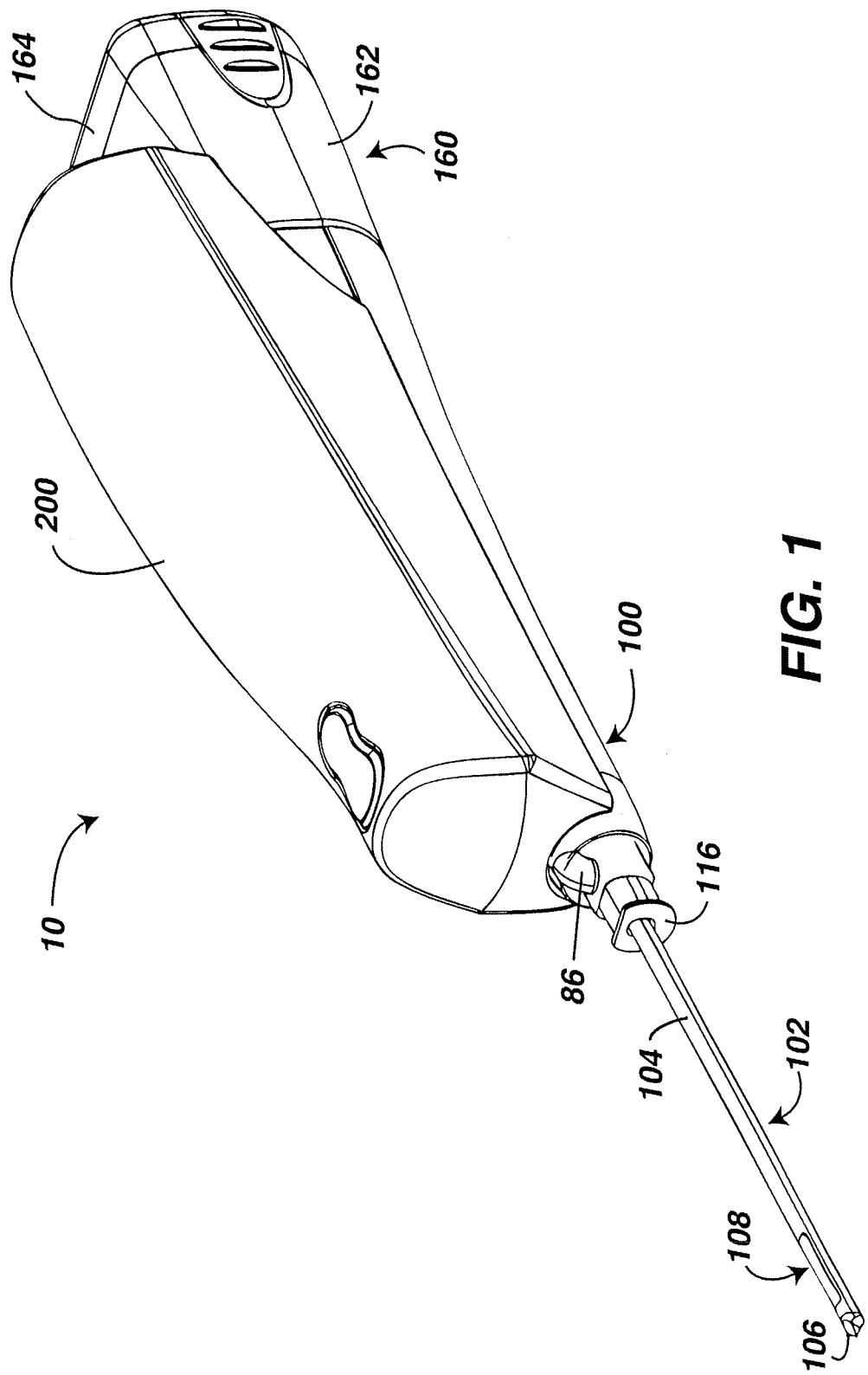
FIG. 1 depicts a perspective view of an exemplary tetherless biopsy device.

As shown in FIG. 1, an exemplary biopsy device (10) comprises a probe (100) and a holster (200). In some embodiments, probe (100) is separable from holster (200). By way of example only, probe (100) may be provided as a disposable component, while holster (200) may be provided as a reusable component.

Use of the term "holster" herein should not be read as necessarily requiring any portion of probe (100) to be inserted into any portion of holster (200). Indeed, in some variations of biopsy device (10), probe (100) may simply sit on holster (200) (e.g., holster (200) acts like a "cradle," etc.), or holster (200) may simply sit on probe (100). In some other variations, a portion of holster (200) may be inserted into probe (100). In either such variations, probe (100) may be secured relative to holster (200) using any suitable structures or techniques (e.g., clips, clasps, snap-fit components, etc.). Furthermore, in some biopsy devices (10), probe (100) and holster (200) may be of unitary or integral construction, such that the two components cannot be separated or are not formed separately. Still other suitable structural and functional relationships between probe (100) and holster (200) will be apparent to those of ordinary skill in the art in view of the teachings herein.

Biopsy device (10) of the present example is configured to be handheld, such that biopsy device (10) may be manipulated and operated by a single hand of a user (e.g., using ultrasound guidance, etc.). However, it will be appreciated in view of the disclosure herein that biopsy device (10) may be used in a variety of other settings (e.g., stereotactic, MRI, etc.) and in other combinations.

In the present example, probe (100) comprises a needle portion (102) and a tissue sample holder (160). Needle portion (102) terminates in a hub (116). Needle portion (102) comprises an outer cannula (104) having a tissue piercing tip (106) and a transverse tissue receiving aperture (108) located proximally from the tissue piercing tip (106). Tissue piercing tip (106) is configured to penetrate tissue without requiring a high amount of force, and without requiring an opening to be preformed in the tissue prior to insertion of tip (106). Suitable configurations for tissue piercing tip (106) will be apparent to those of ordinary skill in the art in view of the teachings herein.

Figure 4:
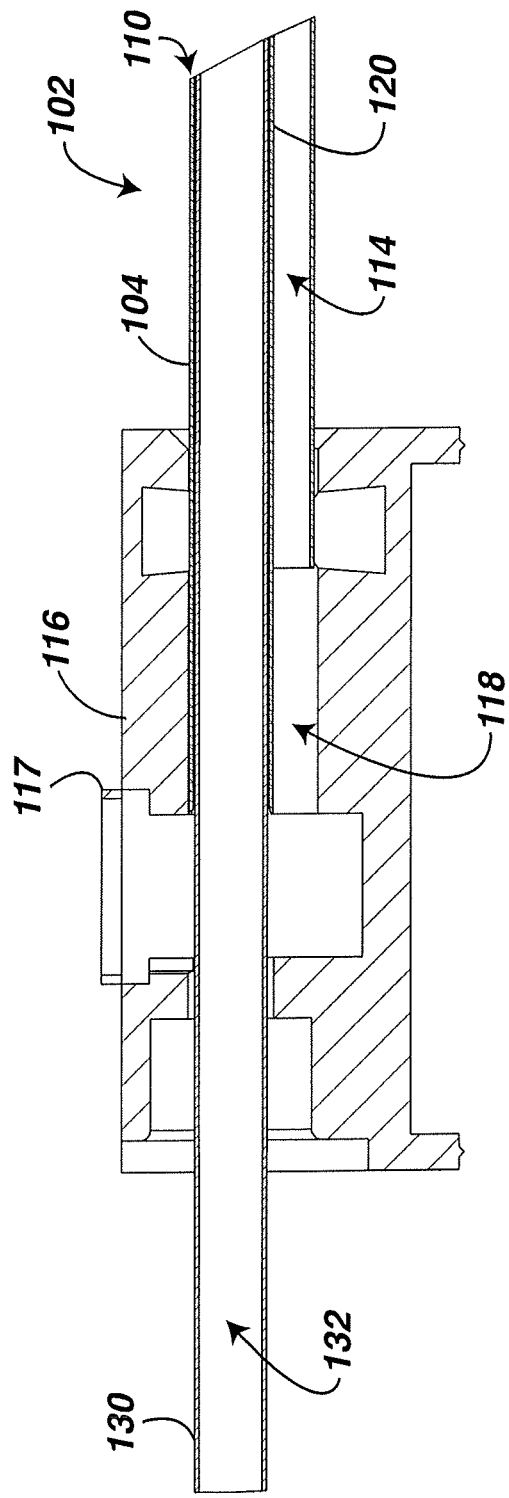
FIG. 4 depicts a cross-sectional view of an exemplary needle hub of the biopsy device of FIG. 1.

As shown in FIG. 4, the interior of outer cannula (104) of the present example defines a first lumen or cannula lumen (110) and a second lumen or vacuum lumen (114), with a wall (120) separating the cannula lumen (110) from the vacuum lumen (114). A plurality of external openings (not shown) are formed in outer cannula (104), and are in fluid communication with vacuum lumen (114). Examples of such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

In some embodiments, wall (120) extends a substantial amount of the length of needle portion (112). In other embodiments, wall (120) proximally extends just past the region where the distal end of a cutter (130), which will be described below, terminates in needle portion (102). For instance, cannula lumen (110) may be sized and configured such that, with cutter (130) disposed therein, a gap exists between the exterior of cutter (130) and at least a portion of the interior of cannula (104). Such a gap may provide a vacuum lumen (114) along the length of cannula (104) proximal to the proximal end of wall (120). Still other ways in which a vacuum lumen (114) may be provided will be apparent to those of ordinary skill in the art in view of the teachings herein.

In the present example, a plurality of transverse openings (not shown) are formed through wall (120) to provide fluid communication between cannula lumen (110) and vacuum lumen (114). Suitable transverse openings are known in the art. The transverse openings in this example are located directly below aperture (108), though one or more of such openings may be located distally or proximally relative to aperture (108). As will be described in greater detail below, vacuum, saline, atmospheric air, and/or pressurized air may be communicated from vacuum lumen (114) to cannula lumen (110) via such transverse openings.

A hollow cutter (130) is disposed within cannula lumen (110). The interior of cutter (130) defines a cutter lumen (132), such that fluid and tissue may be communicated through cutter (130) via cutter lumen (132). As will be described in greater detail below, cutter (130) is configured to rotate within cannula lumen (110) and translate axially within cannula lumen (110). In particular, cutter (130) is configured to sever a biopsy sample from tissue protruding through transverse aperture (108) of outer cannula (104). As will also be described in greater detail below, cutter (130) is further configured to permit severed tissue samples to be communicated proximally through cutter lumen (132). Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system.

In the present example, the axial position of needle portion (102) is substantially fixed relative to the remainder of biopsy device (10). However, other variations may include a needle portion (102) that is axially translatable relative to at least a portion of the remainder of biopsy device (10). For instance, a biopsy device (10) may include a firing mechanism (not shown) that is operable to fire needle portion (102) into tissue. Such a firing mechanism may be spring driven and/or motor driven and/or otherwise driven.

In addition, the angular position of needle portion (102) in the present example is substantially fixed relative to the remainder of biopsy device (10). However, other variations may include a needle portion (102) that is rotatable relative to at least a portion of the remainder of biopsy device (10). For instance, a biopsy device (10) may include a needle rotation mechanism (not shown) that is operable to rotate needle portion (102). Such a needle rotation mechanism may be thumbwheel driven and/or motor driven and/or otherwise driven. Similarly, a thumbwheel may be provided near the interface of needle portion (102) and probe (100), such as at a needle hub (116), for rotation of needle portion (102). Other ways of providing translation and/or rotation of needle portion (102) will be apparent to those of ordinary skill in the art.

Tissue sample holder (160) of the present example is configured to collect tissue samples communicated proximally through cutter lumen (132). In addition, at least a portion of tissue sample holder (160) is removable from probe (100), though tissue sample holder (160) may be non-removable in other versions. In some versions, tissue sample holder (160) comprises a manifold (not shown) that is configured to provide re-directed fluid communication between components of biopsy device (10). For instance, a manifold may re-direct fluid, such as a vacuum, communicated from a vacuum pump (e.g., from vacuum pump (80), described in further detail below) to cutter lumen (132) and/or elsewhere.

In addition, a manifold or other component of tissue sample holder (160) may be rotatable relative to at least some other portion of probe (100). For instance, a manifold or other component of tissue sample holder (160) may include a plurality of tissue sample compartments (not shown), and the manifold or other component of tissue sample holder (160) may be rotatable to successively index each of the tissue sample compartments with cutter lumen (132) to successively capture a discrete tissue sample in each tissue sample compartment. Such rotatability may be provided automatically (e.g., via a motor) and/or manually (e.g., by a user manually rotating a component of tissue sample holder (160), such as a knob). Alternatively, tissue sample holder (160) may be configured such that other components or no components thereof are rotatable.

Tissue sample holder (160) may further comprise an outer cup (162) or other component that is configured to provide a seal for the contents of tissue sample holder (160). Such a cup (162) may be substantially transparent and/or translucent to permit a user to view tissue samples and/or liquid, etc. within tissue sample holder (160). In addition, a tissue sample holder (160) may include trays or strips (not shown) that are removable therefrom. For instance, such trays or strips may define tissue sample compartments, and tissue samples may be removed from tissue sample holder (160) by removing the trays or strips. Such trays or strips may also permit fluid to be communicated therethrough, such that the trays or strips do not obstruct a fluid path between a manifold and cutter lumen (132). Of course, a cup and/or trays or strips may be provided in a variety of alternative ways, or may be omitted altogether.

In still other embodiments, tissue sample holder (160) simply comprises a chamber, without a rotatable manifold or similar components. For instance, tissue sample holder (160) may provide a reservoir-like configuration, and may hold materials such as tissue samples and liquids (e.g., blood, saline, etc.) together. In some variations, a screen, filter, or other structure is provided to facilitate separation of solids from liquids. In addition, one or more filters or other components may be provided to prevent liquids, tissue, etc. from entering vacuum pump (80), which will be described in greater detail below.

Tissue sample holder (160) of the present example comprises a cap (164), which can be removed from cup (162) to access tissue samples within cup (162). The interface between cup (162) and cap (164) may be substantially fluid tight. Other suitable features for cap (164) will be apparent to those of ordinary skill in the art in view of the teachings herein. Alternatively, cap (164) may be omitted.

By way of example only, suitable components for, configurations of, and methods of operating a tissue sample holder (160) are disclosed in U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 20, 2007. The disclosure of each of the above-cited U.S. Patents, U.S. Patent Application Publications, U.S. Provisional Patent Applications, and U.S. Non-Provisional Patent Application is incorporated by reference herein. Still other suitable components for, configurations of, and methods of operating a tissue sample holder (160) will be apparent to those of ordinary skill in the art in view of the teachings herein.

As shown in FIGS. 2-3 and 7-8, a valve manifold (12) and valving member (20) are provided at the proximal end of needle portion (102). Valve manifold (12) of this example comprises three ports (14, 16, 18), each of which is in fluid communication with the hollow interior defined by valve manifold (12). Port (14) is fluidly coupled with a conduit (82), which is also fluidly coupled with vacuum pump (80) via tissue sample holder (160) as described in further detail below. Conduit (82) and port (14) thus provide fluid communication between the interior of valve manifold (12) and vacuum pump (80).

Port (16) is simply open to atmosphere in the present example, such that port (16) provides a vent to the interior of manifold (12). In particular, port (16) simply vents to the interior of holster (200) and/or probe (100). However, port (16) may alternatively vent to atmosphere via a tube (e.g., extending external to holster (200), etc.) or otherwise vent. Port (16) may include one or more filters (not shown), such as an air filter and/or other type of filter.

Port (18) is fluidly coupled with a conduit (86), which is also fluidly coupled with a port (117) of needle hub (116). Conduit (86) and ports (18, 117) thus provide fluid communication between the interior of valve manifold (12) and needle hub (116). In addition, as shown in FIG. 4, needle hub (116) of the present example defines an internal conduit (118), which is in fluid communication with port (117) and with vacuum lumen (114) of needle portion (102). Internal conduit (118) is also in fluid communication with conduit (86) via port (117). Accordingly, the interior of valve manifold (12) may be in fluid communication with vacuum lumen (114) via ports (18, 117), conduit (86), and internal conduit (118) of needle hub (116). In other embodiments, valve manifold (12) is unitarily integral with needle hub (116), such that ports (18, 117) and conduit (86) are not included. Still other ways in which a valve manifold (12) and a vacuum lumen (114) may be placed in fluid communication will be apparent to those of ordinary skill in the art in view of the teachings herein.

While port (14) of the present example is used for providing a vacuum; and port (16) for providing atmospheric venting, it will be appreciated that either port (14, 16) may be used to provide any other desired fluid communication (e.g., pressurized air, saline, vacuum, atmospheric air, etc.). Furthermore, either or both port (14, 16) may be omitted, or additional ports may be added.

As will be described in greater detail below, valving member (20) is configured to selectively provide communication between port (18) and a selected one of ports (14, 16), via the interior of manifold (12). In other words, in the present example, valving member (20) is configured to selectively communicate a vacuum from port (14) to port (18), or atmospheric air from port (16) to port (18), and therefore to vacuum lumen (114).

As shown in FIGS. 2-3 and 7-8, a portion of valving member (20) of the present example is coaxially disposed within valve manifold (12). Valving member (20) is also configured to longitudinally translate within valve manifold (12) and relative to needle portion (102). In particular, the longitudinal position of valve manifold (12) and needle portion (102) are fixed relative to probe (100) in this example. Valve member (20) also includes a plurality of annular seals (38). Seals (38) are configured to provide sealing engagement with valve manifold (12), such that seals (38) prevent fluid (e.g., liquid, vacuum, air, etc.) from passing between seals (38) and the interior wall of valve manifold (12). Seals (38) may comprise a rubber and/or other suitable material(s).

Figure 7:
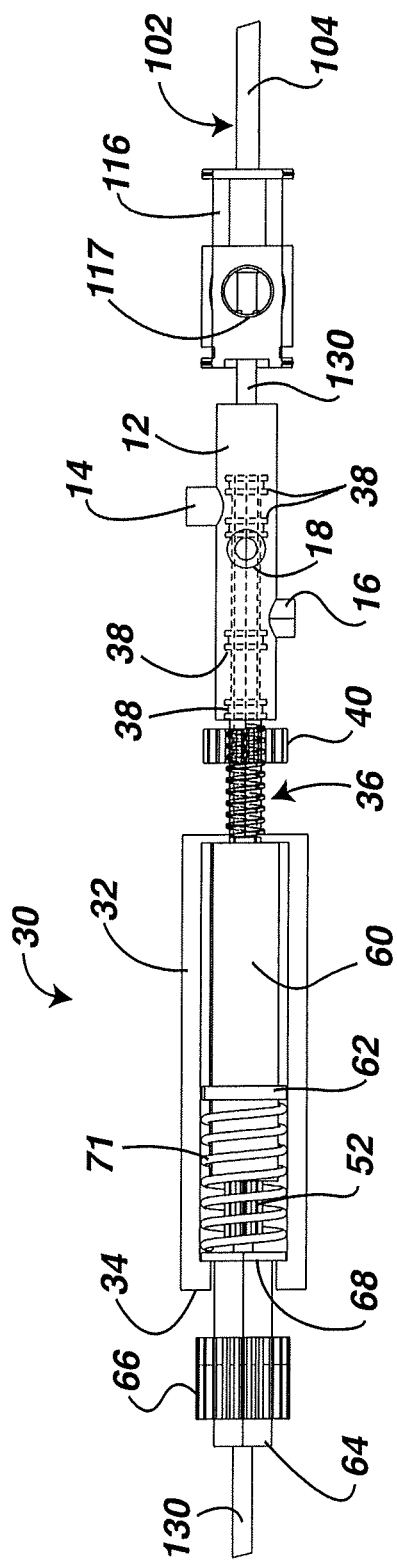
FIG. 7 depicts an exemplary clutching and valving mechanism with the fork member of FIG. 5 in a proximal position.

As described in greater detail below, and with reference to FIGS. 7-8, the longitudinal position of valving member (20) provides selective communication between ports (14, 16, 18). In particular, FIG. 7 shows valving member (20) in a proximal position. In this position, seals (38) provide fluid isolation of port (14). In other words, fluid communicated to port (14) will not pass beyond seals (38) when valving member (20) is in a proximal position in the present example. However, with valving member (20) in a proximal position as shown in FIG. 7, seals (38) permit fluid communication between port (16) and port (18). In particular, with port (16) being open to atmosphere to provide a vent, port (18) will also be vented through valve manifold (12). With port (18) being in fluid communication with vacuum lumen (114) of needle portion (102) as described above, vacuum lumen (114) will be vented through port (16) when valving member (20) is in a proximal position as shown in FIG. 7 in the present example. Thus, one of ordinary skill in the art will immediately recognize that valving member (20) may selectively seal or couple a first port (18) of a plurality of ports (14, 16, 18) relative to a second port (16) of the plurality of ports (14, 16, 18).

Figure 8:
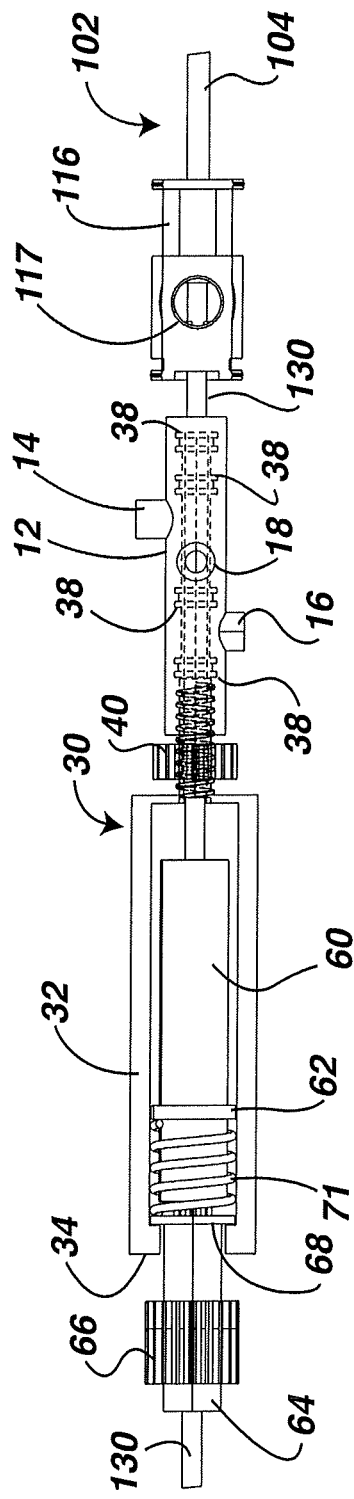
FIG. 8 depicts an exemplary clutching and valving mechanism with the fork member of FIG. 5 in a distal position.

FIG. 8 shows valving member (20) in a distal position. In this position, seals (38) provide fluid isolation of port (16). In other words, atmospheric air communicated to port (16) will not pass beyond seals (38) when valving member (20) is in a distal position in the present example. However, with valving member (20) in a distal position as shown in FIG. 8, seals (38) permit fluid communication between port (14) and port (18). In particular, when vacuum that is induced using vacuum pump (80) is communicated to port (14) via conduit (82), such a vacuum will also be communicated to port (18) through valve manifold (12). With port (18) being in fluid communication with vacuum lumen (114) of needle portion (102) as described above, vacuum will be communicated to vacuum lumen (114) through port (14) when valving member (20) is in a distal position as shown in FIG. 8 in the present example.

Of course, valving member (20), valve manifold (12), ports (14, 16, 18), and seals (38) are merely one example of how vacuum lumen (114) may be selectively vented or placed in communication with a vacuum. It will be appreciated in view of the teachings herein that a variety of alternative structures, mechanisms, and techniques may be used to selectively vary fluid communication to a vacuum lumen (114). Furthermore, while structures will be described below for selectively moving valving member (20) proximally and distally to change the relationship between valving member (20) and valve manifold (12), various other structures, mechanisms, and techniques for providing the same will be apparent to those of ordinary skill in the art in view of the teachings herein.

Figure 6:
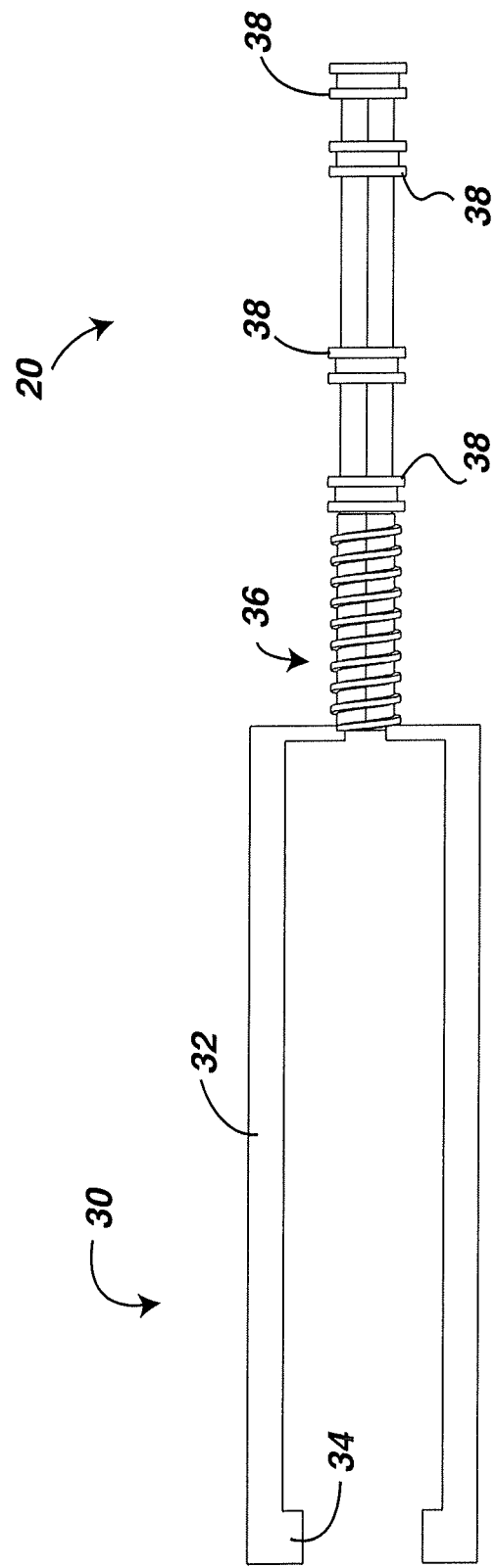
FIG. 6 depicts a plan view of an exemplary fork member of the biopsy device of FIG. 1.

As shown in FIG. 6, fork member (30) extends proximally from the valve member (20) of the present example. In particular, fork member (30) and valve member (20) are integrally formed together in this example. Accordingly, when valve member (20) translates longitudinally in this example, fork member (30) translates therewith, such that fork member (30) and valve member (20) together form a translating member. As shown, fork member (30) includes a pair of proximally extending arms (32), and the proximal end of each arm (32) has an inwardly directed prong (34). As will be described in greater detail below with reference to FIGS. 7-8, prongs (34) are configured to engage a flange (68) upon distal translation of fork member (30).

Fork member (30) further includes a threaded portion (36). A gear (40) is disposed about threaded portion (36). The longitudinal position of gear (40) within biopsy device (10) is substantially fixed in the present example, while gear (40) is configured to rotate within biopsy device (10). Gear (40) includes internal threads (not shown) that are configured to engage the external thread of threaded portion (36). In particular, as gear (40) rotates, the engagement of the threads causes fork member (30) to translate distally or proximally, depending upon the direction of rotation of gear (40). As noted above, such distal or proximal translation of fork member (30) may vary the relationship between valving member (20) and valve manifold (12), thereby varying fluid communication among ports (14, 16, 18) in the present example.

Figure 3:
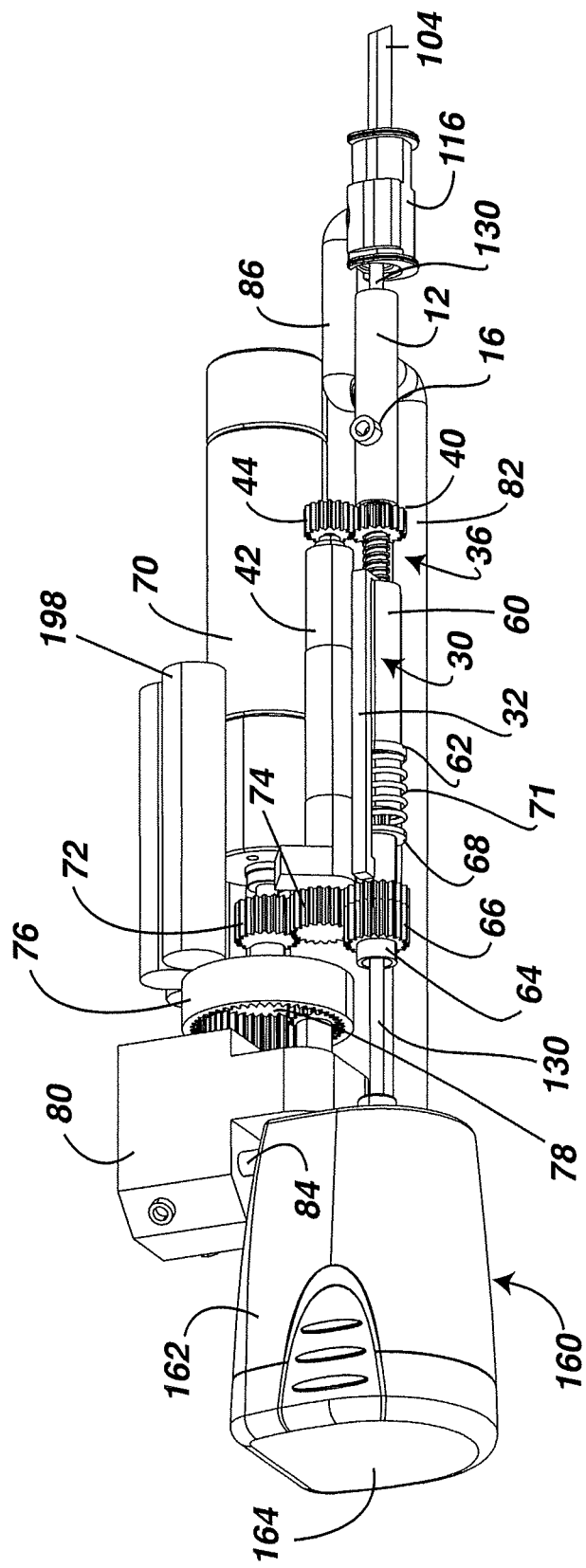
FIG. 3 depicts another partial perspective view of the biopsy device of FIG. 1 with housing components removed.

As shown in FIG. 3, a motor (42) with gear (44) is provided to rotate gear (40). In particular, motor (42) directly drives gear (44), which meshes with gear (40). Accordingly, fork member (30) may be translated distally or proximally, depending upon the direction in which motor (42) is activated to rotate. Of course, any other suitable components, configurations, or mechanisms, may be used to translate fork member (30) distally or proximally. By way of example only, in other embodiments, fork member (30) may be longitudinally driven pneumatically (e.g., by a pneumatic cylinder or actuator, etc.) or by a solenoid.

Figure 5:
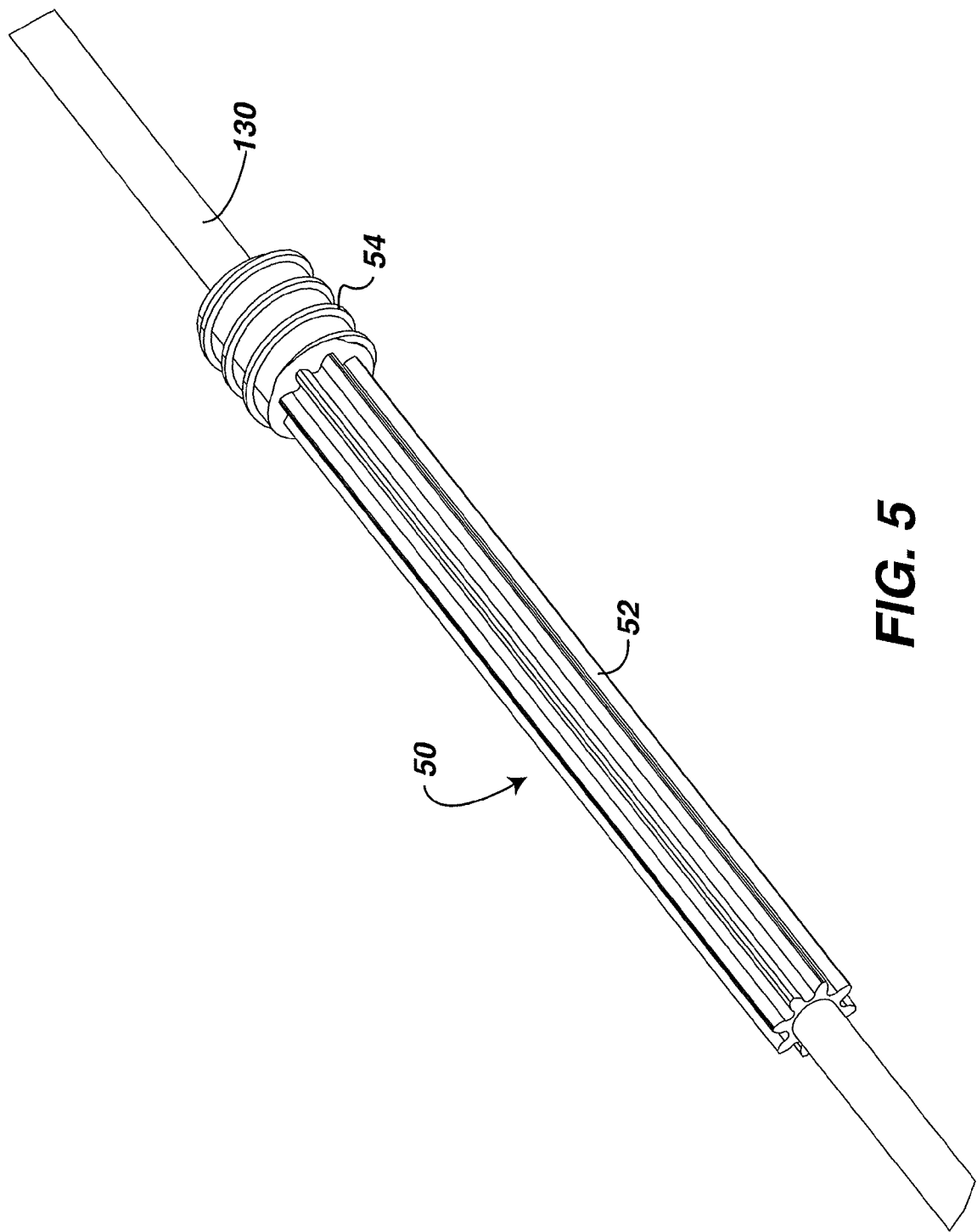
FIG. 5 depicts a perspective view of an exemplary cutter overmold of the biopsy device of FIG. 1.

In the present example, and as shown in FIG. 5, a cutter drive member (50) is provided about cutter (130). In particular, drive member (50) of the present example is overmolded about cutter (130) and is configured to rotate and translate unitarily therewith. In other versions, drive member (50) is secured relative to cutter (130) using other structures or techniques. Drive member (50) of the present example includes a splined portion (52) and a threaded portion (54).

As shown in FIGS. 2-3 and 7-8, a nut (60) is provided about drive member (50). Nut (60) is fixed within biopsy device (10), such that nut (60) is substantially prevented from rotating or translating within biopsy device (10). Nut (60) includes internal threads (not shown) that are configured to engage with the external thread on threaded portion (54) of cutter drive member (50). In particular, nut (60) and drive member (50) are configured such that cutter (130) will translate longitudinally relative to nut (60) (and relative to needle portion (102)) as drive member (50) is rotated, due to engagement of threads of nut (60) and threaded portion (54). The direction of longitudinal translation of cutter (130) depends on the direction of rotation of drive member (50) within nut (60) in this example. Drive member (50) may be rotated through engagement of splined portion (52), as will be described in greater detail below.

A drive gear (64) is provided about cutter (130) in the present example. Drive gear (64) includes a plurality of outer splines (66), an outwardly extending circumferential flange (68), and one or more internal splines (not shown). A spring (71) is provided between flange (68) of drive gear (64) and an outer flange (62) of nut (60). Spring (71) is configured to bias drive gear (64) proximally in this example. Of course any other type of resilient member or any other type of component in any other suitable location may be used to urge drive gear (64) proximally. While spring (71) of the present example is configured to bias flange (68) proximally against prongs (34) of fork member (30), even while fork member (30) is in a proximal position, spring (71) may alternatively have a shorter coiled length, such that flange (68) is not urged into contact with prongs (34) when fork member (30) is in a proximal position. Alternatively, spring (71) may bias drive gear (64) proximally against a feature in the housing (not shown), such that flange (68) is not urged into contact with prongs (34) when fork member (30) is in a proximal position. In such embodiments, suitable longitudinal gaps between flange (68) and prongs (34) when fork member (30) is in a proximal position will be apparent to those of ordinary skill in the art in view of the teachings herein.

As described above, and as illustrated in FIGS. 7-8, rotation of gear (40) by motor (42) may cause fork member (30) to translate distally or proximally, depending upon the direction of rotation of gear (40). With fork member (30) in a proximal position as shown in FIG. 7, drive gear (64) is positioned in its fully proximal position. When cutter (130) is advanced fully distal to "close off" aperture (108) and sever tissue that is prolapsed through aperture (108), splined portion (52) of cutter drive member (50) substantially disengages from drive gear (64), resulting in the termination of cutter (130) rotation and translation. In particular, the internal splines of drive gear (64) are no longer engaged with splined portion (52) of drive member (50). Thus, as drive gear (64) rotates when fork member (30) is in a proximal position, such rotation of drive gear (64) will not be imparted to cutter drive member (50) as the distal end of a cutter (130) reaches the distal end of the aperture (108). In other words, drive gear (64) will simply "freewheel" once the distal end of a cutter (130) reaches the distal end of the aperture (108) while fork member (30) is in a proximal position.

In the present example, when gear (40) is rotated by motor (42) to translate fork member (30) to a distal position, as shown in FIG. 8, such distal translation of fork member (30) will result in distal movement of drive gear (64). In particular, prongs (34) engaged with flange (68) will pull drive gear (64) distally. Such distal movement of drive gear (64) will cause the internal spline(s) of drive gear (64) to engage with splined portion (52) of cutter drive member (50). Upon such engagement, rotation of drive gear (64) will cause concomitant rotation of drive member (50). As described above, due to engagement of threaded portion (54) of drive member (50) with internal threads of nut (60), such rotation of drive member (50) will cause distal or proximal translation of cutter (130), depending on the direction of rotation.

In view of the above, it will be appreciated that drive gear (64), drive member (50), and nut (60) are configured to provide simultaneous rotation and translation of cutter (130). It will also be appreciated in view of the teachings herein that fork member (30) is configured to provide both clutching and valving functions. In particular, fork member (30) is configured to serve as a clutch by selectively engaging drive gear (64) with cutter drive member (50); while also providing valving by repositioning seals (38) of valving member (20) relative to ports (14, 16, 18) of valve manifold (12).

In some embodiments, however, valving member (20) is configured such that fork member (30) may translate through certain longitudinal ranges without affecting the pneumatic level of vacuum lumen (114). For instance, valving member (20) may be configured such that a longitudinal range of travel of fork member (30) that includes a longitudinal position just prior to and during initial stages of engagement between drive gear (64) and cutter drive member (50) has no appreciable effect on the pneumatic level of vacuum lumen (114). Exemplary pneumatic algorithms that may be provided by valving member (20) and valve manifold (12) will be described in greater detail below with reference to FIG. 9.

In the present example, a second motor (70) is provided for rotating drive gear (64). In particular, a first gear (72) is provided on the shaft extending from motor (70). An intermediary gear (74) is positioned between and engaged with first gear (72) and drive gear (64). Accordingly, rotation of motor (70) is communicated to drive gear (64) via meshing gears (72, 74). Of course, any other suitable structures or techniques may be used to drive a drive gear (64) (e.g., belt, chain, etc.). In the present example, splines (66) of drive gear (64) have a sufficient length such that they remain meshed with splines of intermediary gear (74) both when drive gear (64) is in a proximal position (e.g., disengaged from cutter drive member (50) while cutter (130) is advanced fully distal) and when drive gear (64) is in a distal position (e.g., engaged with cutter drive member (50)).

Figure 2:
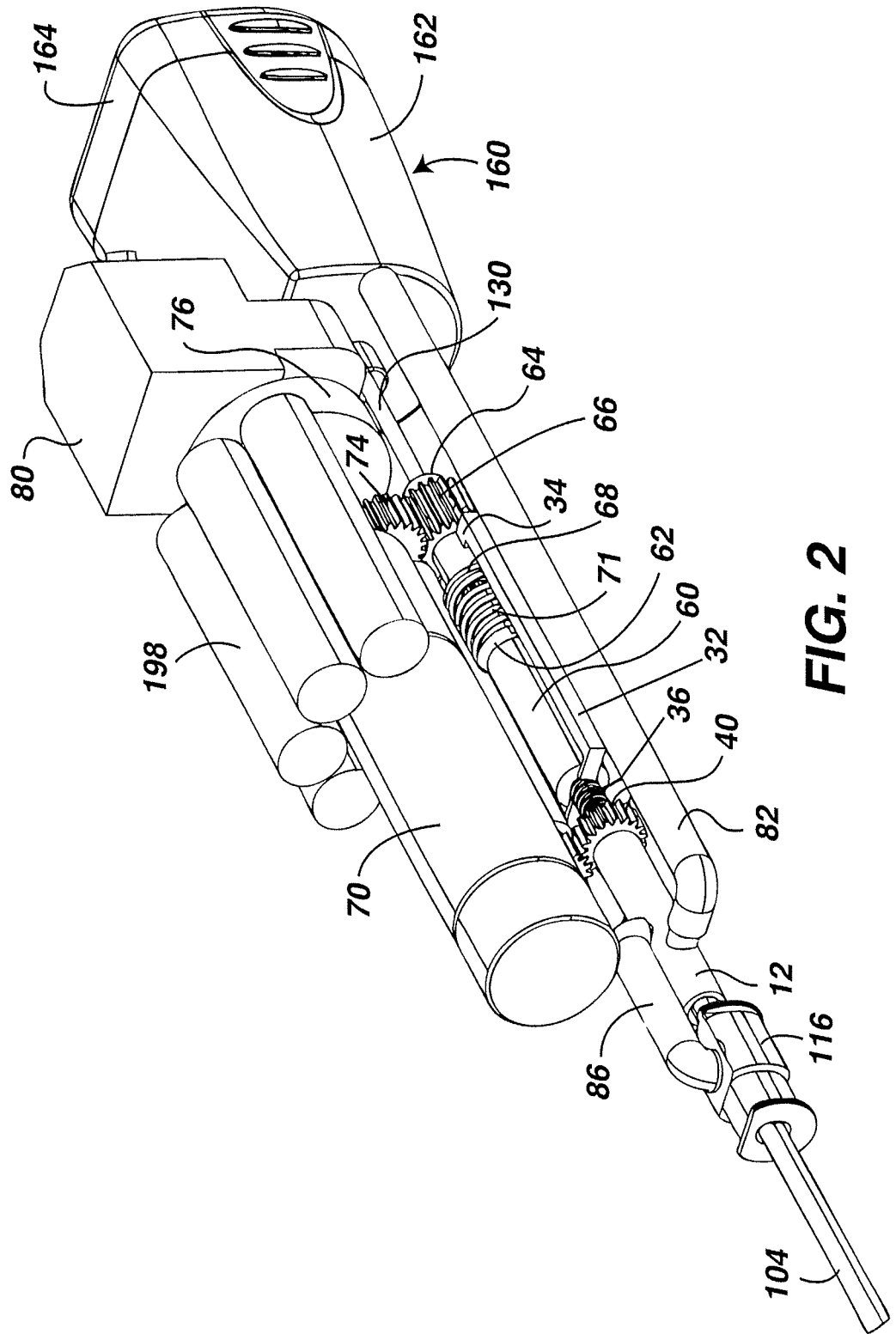
FIG. 2 depicts a partial perspective view of the biopsy device of FIG. 1 with housing components removed.

As shown in FIGS. 2-3, a ring gear (76) is also provided on the shaft extending from motor (70). Ring gear (76) is engaged with a gear (78) extending from vacuum pump (80). Vacuum pump (80) is configured to create a vacuum in response to rotation of gear (78). Suitable internal configurations for vacuum pump (80) to create a vacuum in response to rotation of gear (78) will be apparent to those of ordinary skill in the art in view of the teachings herein.

In addition, vacuum pump (80) of the present example is in fluid communication with the interior of tissue sample holder (160) via a port (84). Conduit (82) is also in communication with the interior of tissue sample holder (160). Tissue sample holder (160) is thus configured such that a vacuum communicated to tissue sample holder (160) by vacuum pump (80) via port (84) will be further communicated to vacuum conduit (82). As described above, a vacuum communicated to vacuum conduit (82) may further be communicated to vacuum lumen (114), depending on the longitudinal position of valving member (20) within valve manifold (12).

In the present example, cutter lumen (132) is also in fluid communication with the interior of tissue sample holder (160). Accordingly, a vacuum created within tissue sample holder (160) by vacuum pump (80) is communicated to cutter lumen (132) in addition to being communicated to conduit (82).

Of course, a vacuum may alternatively be created using a variety of alternative structures, devices, and techniques, and may be communicated along a variety of alternative paths using any suitable structures, devices, and techniques.

It will be appreciated in view of the teachings herein that motor (70) may continue to drive or charge vacuum pump (80), even while drive gear (64) is disengaged from cutter drive member (50). For instance, such "idle" charging of vacuum pump (80) may be desirable when multiple tissue samples are being taken during a single insertion of needle portion (102) within a patient. In other words, a user may wait to let motor (70) charge vacuum pump (80) between sampling cycles, even while needle portion (102) remains inserted within a patient. During this time, the cutter (130) may be advanced distally, "closing off" aperture (108), and the user may reposition biopsy device (10) (e.g., by rotating needle portion (102) within patient to re-orient aperture (108)).

In view of the above, it will be appreciated that a first motor (42) may be used to selectively translate fork member (30) distally or proximally, depending on the direction of rotation of motor (42), in order to provide simultaneous clutching and valving functions (among other potential functions). It will also be appreciated that a second motor (70) may be used to simultaneously drive a drive gear (64) and vacuum pump (80). Those of ordinary skill in the art will appreciate in view of the teachings herein, however, that a single motor may be used to serve all such functions and/or other functions. For instance, one or more clutches may be added to selectively engage a variety of gears or other components with one or more drive shafts or drive gears. In addition, while motors (42, 70) of the present example are electrical, driven by batteries (198), motors (42, 70) may alternatively comprise one or more pneumatic motors, pneumatic actuators, or other devices.

To the extent that batteries (198) are used, such batteries may be rechargeable or non-rechargeable. In some alternate embodiments, biopsy device (10) receives power via wires from an external power source. In other embodiments, biopsy device (10) receives power from a separate source wirelessly. In still other embodiments, biopsy device (10) receives power from a source of pressurized medium (e.g., an on-board manual pump, a separate pump connected to biopsy device (10) via a conduit, etc.). It will also be apparent to those of ordinary skill in the art in view of the teachings herein that biopsy device (10) of the present example is tetherless, such that no wires, conduits, tubes, or other components need to be connected to biopsy device (10) in order for it to function fully. In other words, biopsy device (10) is substantially portable, and may be used in a variety of settings. Of course, other variations of biopsy device (10) may include one or more tethers, such as a wire, cable, tube, etc. In addition, motors (42, 70), batteries (198), and vacuum pump (80) in the present example are located within re-usable holster (200) of biopsy device (10). However, other variations may include any or all such components in disposable probe (100) or elsewhere. Still other suitable components and arrangements of components for variations of biopsy device (10) will be apparent to those of ordinary skill in the art in view of the teachings herein.

Figure 9:
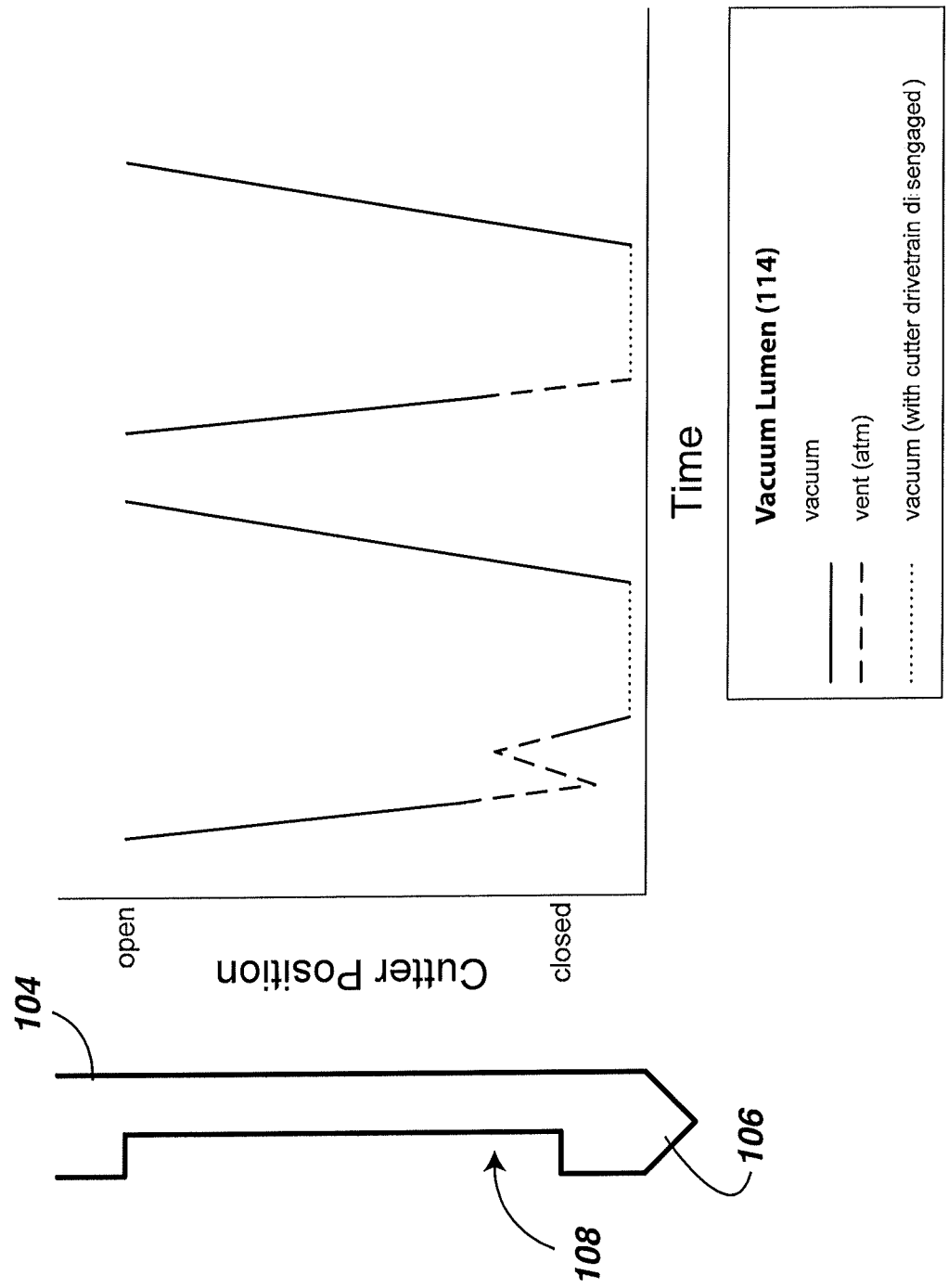
FIG. 9 depicts an exemplary timing algorithm that may be used for providing fluid communication to a vacuum lumen as a function of cutter position.

FIG. 9 depicts examples of how fluid may be communicated to vacuum lumen (114) as a function of both the longitudinal position of cutter (130) and time. Such pneumatic algorithms may be provided by selective motor (42) activation, which may be used to selectively vary the longitudinal position of valve member (20) within valve manifold (12). Of course, variation of the longitudinal position of cutter (130) may be provided by selective motor (70) activation in conjunction with clutching by fork member (30) as described above. As shown, the pneumatic algorithms begin with the cutter (130) being retracted proximally, such that aperture (108) is "open." It will be appreciated, however, that cutter (130) may actually be advanced distally to "close" aperture (108) when needle portion (102) is inserted into a patient's breast. In other words, the cutter (130) may be retracted proximally, and the illustrated pneumatic algorithms initiated, after needle portion (102) has been inserted into a patient's breast.

In the present example, a vacuum is communicated to vacuum lumen (114) before cutter (130) begins translating distally, thereby drawing tissue into aperture (108). As shown, a vacuum may continue to be communicated to vacuum lumen (114) as cutter (130) moves toward a distal position, retaining tissue drawn into aperture (108). As cutter (130) approaches a distal position, vacuum lumen (114) may be vented, during which time cutter (130) is severing tissue. Cutter (130) may reciprocate one or more times near the distal edge of aperture (108) with a vent continuing to be provided to vacuum lumen (14). Cutter (130) may then be advanced distally to a degree sufficient to "close off" aperture (108). Concurrently, drive gear (64) disengages from drive member (50), leaving cutter (130) in a distal position and no longer rotating or translating. While cutter (130) is in a distal position, vacuum may again be communicated through vacuum lumen (114). At this time, a vacuum communicated through cutter lumen (132) may draw a tissue sample severed by cutter (130) proximally into tissue sample holder (160). Drive gear (64) may then be re-engaged with drive member (50), rotating in a different direction to translate cutter (130) proximally. A vacuum may again be communicated to vacuum lumen (114) as cutter (130) is retracted, thereby drawing additional tissue into aperture (108) for subsequent sampling. The process may be repeated until a desired number of tissue samples are obtained. Vacuum may be communicated through cutter lumen (132) throughout the entire process, or otherwise.

As is also shown, reciprocation of cutter (130) during a sampling cycle is merely optional. In other words, a cutter (130) may simply travel distally to sever a tissue sample in one motion, then remain in a distal position while the tissue sample travels proximally through cutter lumen (132) (and while vacuum pump (80) recharges, etc.), then travel proximally to permit a subsequent tissue sample to be taken. Other ways in which cutter (130) motion may be provided, as well as ways in which pneumatic communication may be provided to vacuum lumen (114) and/or cutter lumen (132) as a function of cutter position (130) or otherwise, will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy device, wherein the biopsy device comprises:
   (a) a needle, wherein the needle comprises:
      (i) a closed tip,
      (ii) a first lumen configured to receive a cutter, and
      (iii) a transverse tissue receiving aperture in fluid communication with the first lumen, wherein the transverse tissue receiving aperture is proximal to the closed tip;
   (b) a handpiece, wherein the needle extends distally from the handpiece;
   (c) a vacuum pump, wherein the vacuum pump is positioned within the handpiece;
   (d) a cutter, wherein the cutter is rotatable and translatable within the first lumen of the needle to sever tissue protruding through the transverse tissue receiving aperture, wherein the cutter defines a cutter lumen; and
   (e) a single motor, wherein the single motor is operable to simultaneously:
      (i) drive the vacuum pump to draw a vacuum through the cutter lumen,
      (ii) rotate the cutter within the first lumen of the needle, and
      (iii) translate the cutter within the first lumen of the needle.

2. The biopsy device of claim 1, wherein the needle further comprises a needle hub and a second lumen, wherein the second lumen is in fluid communication with the first lumen, wherein the needle hub comprises an opening in fluid communication with the second lumen.

3. The biopsy device of claim 2, further comprising a conduit in fluid communication with the opening of the needle hub.

4. The biopsy device of claim 3, further comprising a valving assembly, wherein the valving assembly comprises a manifold, wherein the conduit is further in fluid communication with the manifold.

5. The biopsy device of claim 4, wherein the valving assembly further comprises a valving member configured to translate longitudinally within the manifold, wherein the valving member is configured to redirect fluid communication within the manifold as a function of the longitudinal position of the valving member within the manifold.

6. The biopsy device of claim 5, wherein the longitudinal position of the valving member within the manifold is based at least in part on the longitudinal position of the cutter within the first lumen.

7. The biopsy device of claim 2, further comprising a clutching and valving mechanism, wherein the clutching and valving mechanism is configured to provide selective fluid communication to the second lumen and provide selective engagement between the cutter and the single motor.

8. The biopsy device of claim 7, further comprising a second motor, wherein the clutching and vavling mechanism are driven by a second motor.

9. The biopsy device of claim 1, further comprising a clutching mechanism, wherein the clutching mechanism is configured to selectively provide communication from the single motor to the cutter.

10. The biopsy device of claim 1, wherein the closed tip of the needle is configured to pierce tissue.

11. The biopsy device of claim 1, wherein the single motor is positioned within the handpiece.

12. A biopsy device, wherein the biopsy device comprises:
 (a) a needle, wherein the needle comprises:
  (i) a closed tip,
  (ii) a first lumen configured to receive a cutter,
  (iii) a transverse tissue receiving aperture in fluid communication with the first lumen, wherein the transverse tissue receiving aperture is proximal to the closed tip, and
  (iv) a second lumen, wherein the second lumen is in fluid communication with the first lumen;
 (b) a handpiece, wherein the needle extends distally from the handpiece;
 (c) a cutter, wherein the cutter is rotatable and translatable within the first lumen of the needle to sever tissue protruding through the transverse tissue receiving aperture, wherein the cutter defines a cutter lumen;
 (d) a vacuum pump, wherein the vacuum pump is positioned within the handpiece, wherein the vacuum pump is in fluid communication with the cutter lumen; and
 (e) a single motor, wherein the single motor is positioned within the handpiece, wherein the single motor is operable to simultaneously:
  (i) drive the vacuum pump to draw a vacuum through the cutter lumen,
  (ii) rotate the cutter within the first lumen of the needle, and
  (iii) translate the cutter within the first lumen of the needle.

13. The biopsy device of claim 12, further comprising a valving mechanism configured to selectively redirect fluid communication to the second lumen, wherein the valving mechanism is located within the handpiece.

14. The biopsy device of claim 13, wherein the valving mechanism comprises a manifold and a valving member within the manifold.

15. The biopsy device of claim 14, wherein the manifold comprises a plurality of ports, wherein the valving member is configured to selectively provide fluid communication between two or more of the ports as a function of longitudinal position of the valving member within the manifold.

16. The biopsy device of claim 15, wherein the vacuum pump is in fluid communication with at least one port of the manifold.

17. The biopsy device of claim 12, further comprising a clutching mechanism configured to selectively engage the single motor with the cutter.

18. The biopsy device of claim 12, further comprising a tissue sample chamber, wherein the vacuum pump is further in fluid communication with the tissue sample chamber such that the vacuum pump is in fluid communication with the cutter lumen via the tissue sample chamber.

19. The biopsy device of claim 12, further comprising one or more batteries positioned within the handpiece, wherein the one or more batteries are in communication with the single motor to provide power to the single motor.

20. A biopsy device, wherein the biopsy device comprises:
 (a) a probe portion, wherein the probe portion comprises:
  (i) needle having a tip, a lumen, and a transverse tissue receiving aperture in fluid communication with the lumen of the needle,
  (ii) a cutter, wherein at least part of the cutter is positioned within the lumen of the needle, and
  (iii) a cutter drive assembly, wherein the cutter drive assembly is operable to rotate and translate the cutter in within the lumen of the needle to sever tissue protruding through the transverse tissue receiving aperture; and
 (b) a holster portion, wherein the probe portion and the holster portion are configured to couple together to form a handheld assembly, wherein the holster portion comprises:
  (i) a vacuum pump configured to communicate with the cutter lumen,
  (ii) a single motor operable to drive the vacuum pump, and
  (iii) a drive member coupled with the single motor, wherein the drive member is further configured to couple with the cutter drive assembly such that the single motor is operable to drive the cutter drive assembly via the drive member to thereby simultaneously rotate and translate the cutter while further simultaneously driving the vacuum pump.

* * * * *

UNITED STATES PATENT AND TRADEMARK OFFICE
CERTIFICATE OF CORRECTION

PATENT NO.         : 8,454,532 B2
APPLICATION NO.    : 12/944037
DATED              : June 4, 2013
INVENTOR(S)        : John A. Hibner Page 1 of 1

It is certified that error appears in the above-identified patent and that said Letters Patent is hereby corrected as shown below:

In the Claims:

Column 13, Claim 8, line 3, reads "...a second motor..."; which should be deleted and replaced with "...the second motor...."

Column 14, Claim 15, lines 2-3, read "...of longitudinal position..."; which should be deleted and replaced with "...of a longitudinal position...."

Column 14, Claim 20, line 21, reads "...(i) needle having..."; which should be deleted and replaced with "...(i) a needle having...."

Column 14, Claim 20, lines 35-36, read "...the cutter lumen..."; which should be deleted and replaced with "...the lumen...."

Signed and Sealed this
Twentieth Day of August, 2013

Teresa Stanek Rea
*Acting Director of the United States Patent and Trademark Office*